United States Patent [19]

Meyer et al.

[11] Patent Number: 4,979,644
[45] Date of Patent: Dec. 25, 1990

[54] RATE-CONTROLLED GRAVITY DRIP DELIVERY APPARATUS

[75] Inventors: Jack E. Meyer, Dallas; Thomas C. Thompson; Tamera L. Clark, both of McKinney; Andrew P. Johnson, Garland; Don M. Killman, Balch Springs, all of Tex.

[73] Assignee: Quest Medical Inc., Dallas, Tex.

[21] Appl. No.: 311,701

[22] Filed: Feb. 15, 1989

[51] Int. Cl.$^5$ .................................... B65D 35/22
[52] U.S. Cl. ...................... 222/94; 222/129; 222/145
[58] Field of Search ............ 222/94, 129, 145, 181, 222/478, 105, 204, 464; 137/599; 604/251

[56] References Cited

U.S. PATENT DOCUMENTS

| | | | |
|---|---|---|---|
| 3,202,324 | 8/1965 | Honnet et al. | 222/181 |
| 3,298,367 | 1/1967 | Bergman | 137/599 |
| 3,490,656 | 1/1970 | Taschner | 222/464 |
| 3,896,972 | 7/1975 | Neidore et al. | 222/136 |
| 4,113,149 | 9/1978 | Harsch | 222/181 |
| 4,191,183 | 3/1980 | Mendelson | 222/145 |
| 4,830,235 | 5/1989 | Miller | 222/481.5 |

Primary Examiner—Andres Kashnikow
Assistant Examiner—W. Todd Waffner
Attorney, Agent, or Firm—Ross, Howison, Clapp & Korn

[57] ABSTRACT

An apparatus for rate controlled gravity drip delivery of a liquid from a replaceable storage container to a delivery site includes a first mount for removably suspending the container at a first elevation higher than the site. A second mount is located above the site, but at a second elevation below the first elevation by a predetermined amount. The second mount carries an intersurface comprising a venting tubing connector having an outlet into a delivery conduit extending to the site. A metering tube of predetermined flow resistance substantially higher than that of the delivery conduit extends from the container at one end and is releasably secured to the connector at its other end to define a two part flow path from the container to the site through the metering tube and delivery conduit. The venting of the connector subjects the fluid at the connector to the same ambient pressure as the fluid in the container so that the rate of delivery is substantially predetermined by the difference in the first and second elevations and flow resistance of the metering tube.

7 Claims, 4 Drawing Sheets

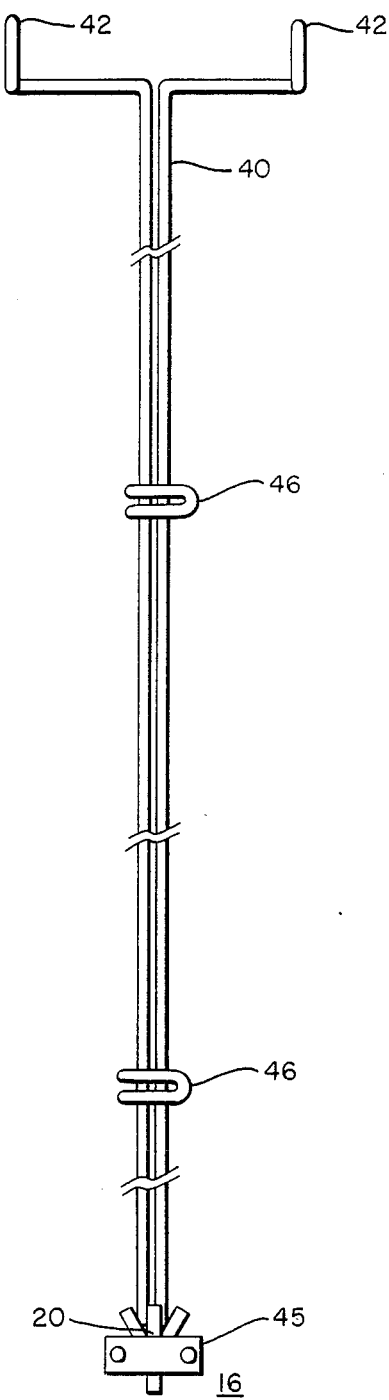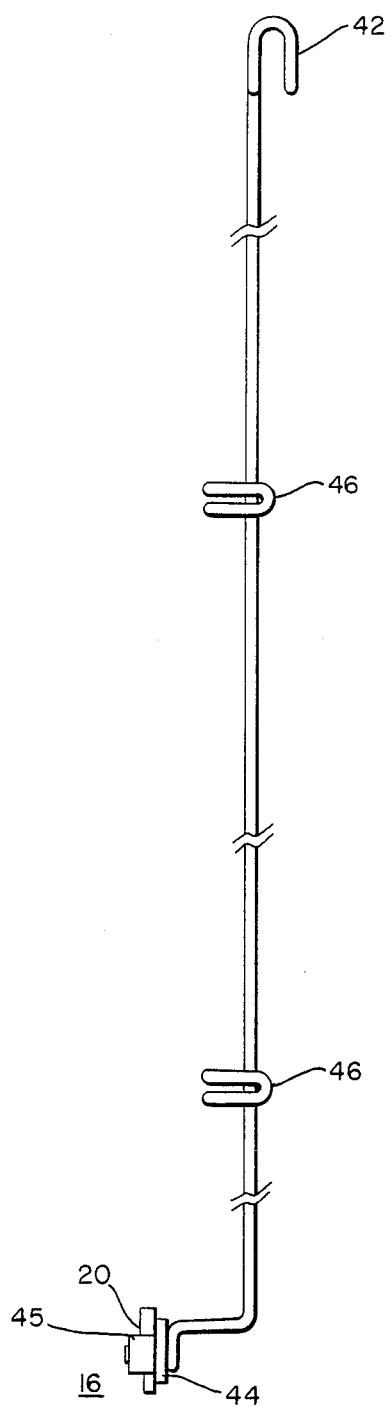

RATE-CONTROLLED GRAVITY DRIP DELIVERY APPARATUS

TECHNICAL FIELD OF THE INVENTION

This invention relates to apparatus for the delivery of liquids at slow steady predetermined rates under the influence of gravity.

BACKGROUND OF THE INVENTION

Industrial or commercial operations often have a need for simple systems to provide a slow steady delivery of a liquid to a receptacle or other delivery site. An example of such a need arises in the gradual dispensing of degreasing bacteria solution into grease traps such as found in restaurants. One commercial vendor of such bacteria solutions has provided for the dispensing of its fluids by means of a peristaltic pump. Use of such a pump involves the expense of the pumping instrument, and also requires continued attention and maintenance, as well as training of relatively unskilled workers in the operation of the pump. The invention of this application provides a very simple and inexpensive mechanism for implementing steady slow drip delivery of liquids at predetermined average rates, with a minimum of complexity in its utilization so as to render its use efficient and reasonably foolproof.

SUMMARY OF THE INVENTION

In accordance with the invention, there is provided apparatus for rate-control of gravity drip delivery of a liquid from a replaceable storage container to a site which includes a first mount for removably suspending the container at a first elevation higher than the site. A second mount located at a second elevation higher than the site is fixed below the first elevation by a predetermined amount, and an interface is secured to the second mount. A delivery conduit extends from the interface to the site of desired delivery. A metering tube having a predetermined flow resistance substantially higher than that of the delivery conduit extends from the container at one end and is releasably secured to the interface at the other end establishing a two part flow path from the container to the site through the metering tube and delivery conduit. A flow resistance separator is provided for the interface to subject the fluid at the interface to substantially the same ambient pressure as the fluid in the container, so that the average rate of delivery is substantially predetermined by the difference of the first and second elevations and the flow resistance of the metering tube. The flow rate is substantially independent of the length of the delivery conduit and the height of the container above the site. The system may be employed to deliver the liquid at integral multiples of the predetermined average delivery rate by providing a first mount which may removably secure a plurality of the liquid containers at the first elevation, and a plurality of metering tubes extending from the containers to the interface, which acts as a manifold for gathering the individual metered flows into the delivery conduit.

The invention contemplates the use of a mounting bracket for holding the flow path elements of the system which includes a hanger adapted to being secured to a wall to releasably hold a plurality of collapsible containers. A vertical element is secured to the hanger so that it depends vertically therefrom, and carries a vented interface manifold at a fixed elevation below the hanger. The vented manifold has a plurality of inlets adapted to receive the distal ends of the metering tubes remote from the containers, and an outlet carrying the delivery conduit which extends to the delivery site.

In one aspect, the invention includes a replaceable delivery apparatus for use with a container hanger fixed at a predetermined vertical distance above a vented interface which has its outlet communicating with a delivery conduit. The replaceable delivery apparatus includes a flexible container containing the liquid to be delivered and adapted to be suspended on the hanger. A metering tube having a predetermined flow resistance substantially higher than that of the delivery conduit extends from one end of the container in communication with the interior of the container. At its other end, the metering tube is adapted to releasable securement in the vented interface. In use, the container is hung on said mounting and its metering tube is secured in the interface, so that the liquid will be delivered from the container at an average rate substantially determined by the said predetermined vertical distance and the flow resistance of the metering tube.

BRIEF DESCRIPTION OF THE DRAWINGS

FIG. 3 is a front view of a vertical element to cooperate with the hanger of FIG. 2;

FIG. 4 is a side view of the vertical element shown in FIG. 3;

DETAILED DESCRIPTION OF THE INVENTION

Figure 1:
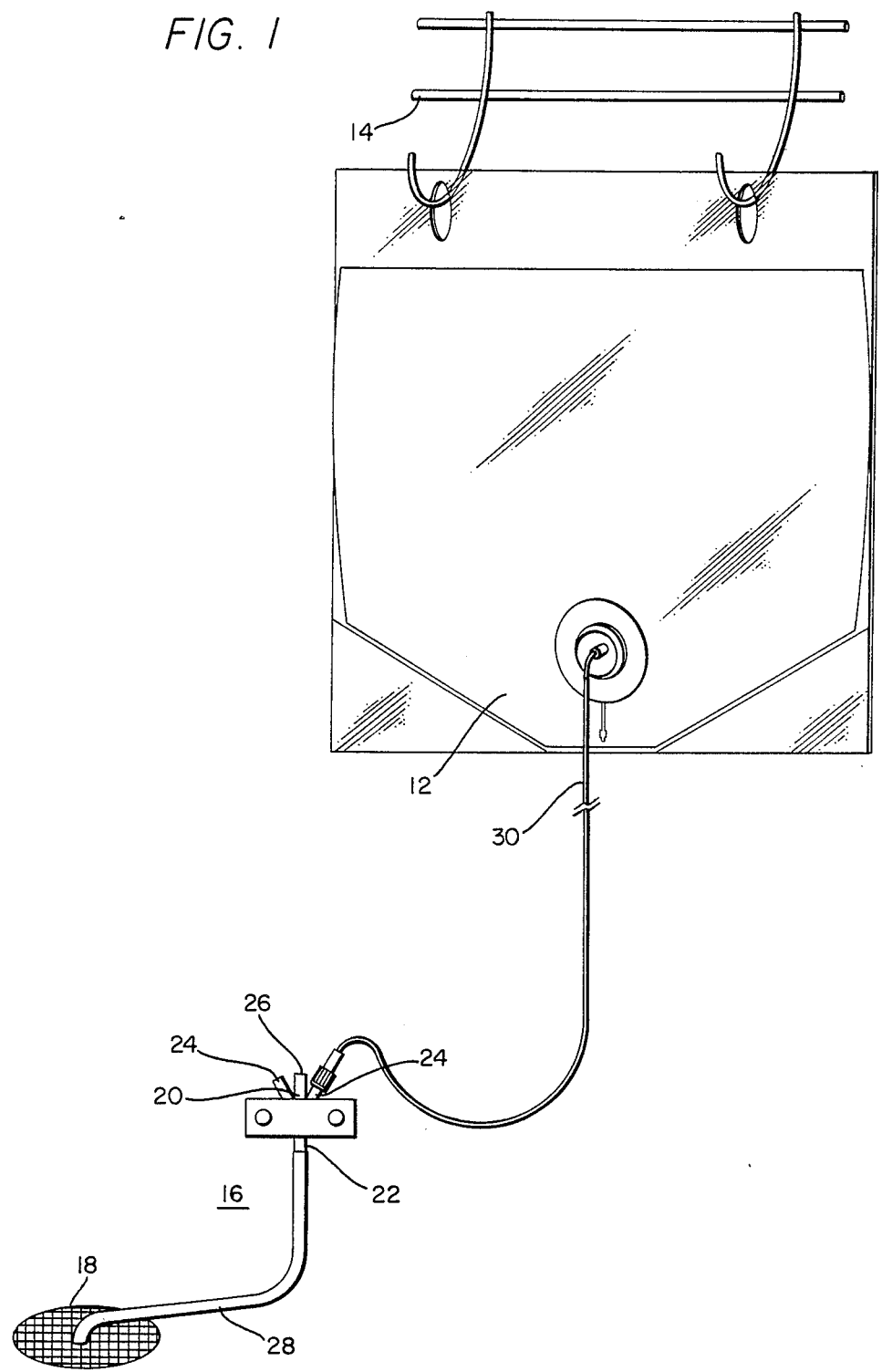
FIG. 1 is a schematic illustration of apparatus embodying the present invention.

In the schematic illustration of the present invention shown in FIG. 1, a collapsible storage container 12 such as a flexible bag containing the liquid to be delivered is suspended from first mounting means 14 comprised of hooks which are fixedly secured at a first elevation. A second mounting means 16 is secured at a second elevation below container 12. The vertical drop from hook mounting 14 to mount 16 is predetermined. Mount 16 is situated above a delivery site indicated by the numeral 18, which may be a grease trap or other receptacle or conduit to which the fluid is to be delivered. The amount of vertical drop from mount 16 to site 18, or from container 12 to site 18, is not critical.

A flow manifold interface 20 is fixedly secured by mount 16. Interface 20 may be a simple tri-site connector such as used conventionally in intravenous tubing systems. The interface 20 includes an outlet 22, a plurality of inlet ports 24 and an air vent 26. Air vent 26 serves to isolate the flow resistance of the system upstream from interface 20. A relatively large delivery conduit 28 extends from interface outlet 22 to the receptacle 18. Delivery conduit 28 is selected to be large enough to present essentially no flow resistance for trickles of fluid at the rates to be delivered to receptacle 18. A metering tube 30 extends from container 12, having communication with the liquid contents thereof, and is removably secured to one of the inlet ports 24 of interface 20. The flow resistance of metering tube 30 is correlated with the head height provided between container 12 and interface 20 by mounts 14 and 16. This flow resistance may be provided by any suitable control element including a restricted orifice. Most conveniently, it is simply determined by a relatively small inner diameter of tubing 30 in conjunction with the length of tubing 30. By correlating the flow resistance of tubing and the head height, and by exposing the fluid to substantially the same ambient pressure at container 12 and at connector 20 through air vent 26, the average rate of delivery of liquid through metering tube 30 to the connector 20 is predetermined. The flow rate characteristic of the entire system is, in effect, established by the isolation of the tubing 30.

While the gradual depletion of the liquid contents of container 12 will have an effect on delivery rate due to decreasing head height, this invention contemplates a flow resistance for metering tube 30 to provide the average desired delivery rate over the time of delivery of the entire contents of the container. Variations from the average rate can be minimized by minimizing the difference in elevation of the full level and almost empty level of container 12, as well as by increasing the vertical drop between fixed mounts 14 and 16 or increasing the flow resistance between container 12 and interface 20, as by lengthening tube 30 or decreasing its diameter.

In one specific application of this invention, a system for delivering grease digestant solution at an approximate average rate of fourteen fluid ounces per day has been utilized. The appropriate delivery rate has been achieved by providing an approximate four foot drop between container 12 and interface 20, and by utilizing microbore intravenous tubing having an inner diameter of 0.016 inches (±0.001inch) and a length of six feet. The system so configured delivers an average rate as desired with an approximate 10% variation above and below the average rate from container full to container empty.

Because of the isolation of the flow resistance presented between container 12 and interface 20, by means of air vent 26, the rate of delivery to receptacle 18 is substantially predetermined by the preset elevation drop between mounts 14 and 16 and the predetermined configuration of the metering tube 30. In the example given, a delivery conduit 28 of approximately one eighth inch inner diameter is sufficiently large to receive flows at such rates, and at multiples of several times such rates, without introducing significant flow resistance.

A plurality of ports 24 are provided on interface 20 so that integral multiples of the rate established by delivery from one container 12 may be delivered to delivery conduit 28 by the simple procedure of hanging multiple containers and connecting them to the multiple inlet ports 24.

Figure 2:
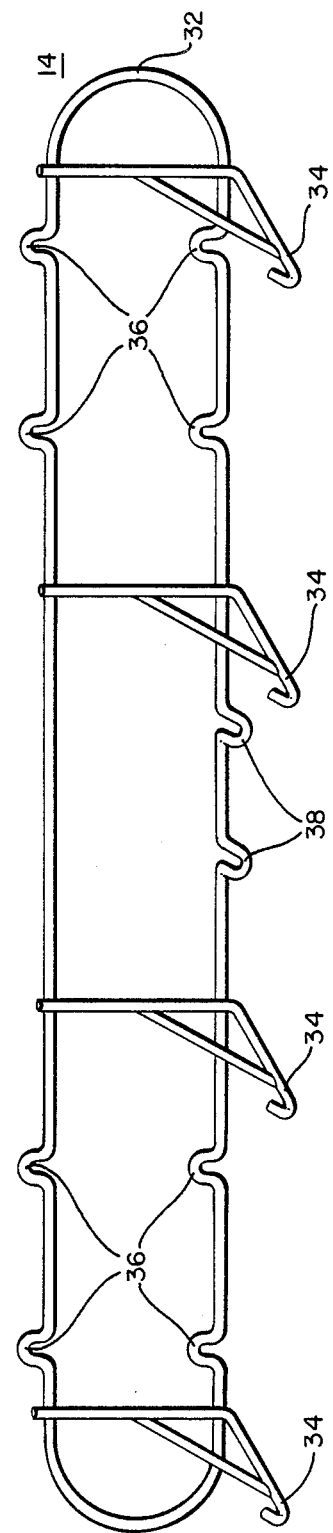
FIG. 2 is a perspective view of a hanger for wall mounting which may be utilized in the present invention.

FIGS. 2–4 illustrate a simple and inexpensive mounting bracket system for establishing the desired head differential as one element in predetermining the average flow rate. FIG. 2 depicts a mount 14 formed by a lateral bracket 32 carrying a plurality of horizontally spaced hooks 34. Bracket 32 is formed from wire, with crimped portions 36 by which the bracket may be mounted to a wall with screws. Hooks 34 may be secured to the bracket 32 by spot welding. Bracket 32 also carries a pair of spaced downwardly facing crimped portions 38 from which may be suspended the vertical element 40 illustrated in FIGS. 3 and 4.

Vertical element 40 is also formed from wire, and includes spaced upper hooks 42 adapted to be placed in and retained by crimped portions 38 on bracket 32. In this way, vertical element 42 may be installed in a fixed orientation with respect to bracket 32. The lower end of vertical element 40 carries a clamp plate 44 which in turn carries clamp 45 holding the manifold interface 20. Tubing clips 46 may be spaced along the length of vertical element 40 in order to retain metering tube or tubes 30.

Figure 5:
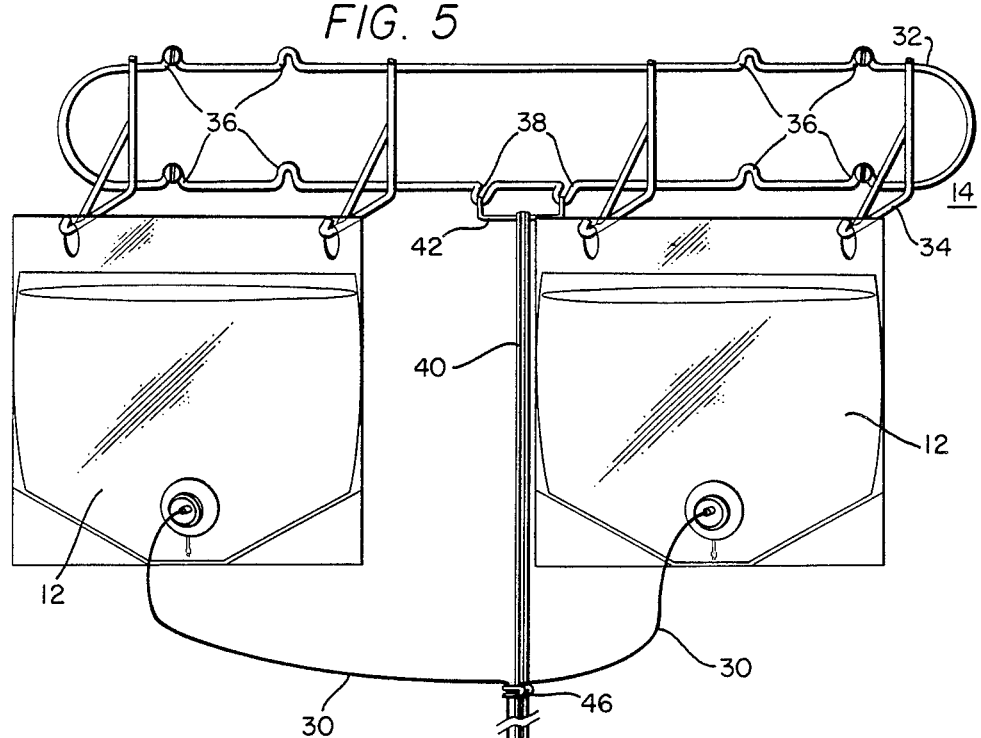
FIG. 5 illustrates use of the hanger and vertical element of FIGS. 2-5 in a system assembled in accordance with the invention.

An exemplary installation of this invention utilizing the hanger bracket and vertical element is shown in FIG. 5. In this example, two containers are shown suspended and connected at the system to provide twice the delivery rate which one would provide. Of course, the system may receive only a single container, or a longer hanger may be provided to accommodate even larger multiples of a single unit delivery rate, by suspending more containers connected to a corresponding number of inlet ports on interface 20.

Figure 6:
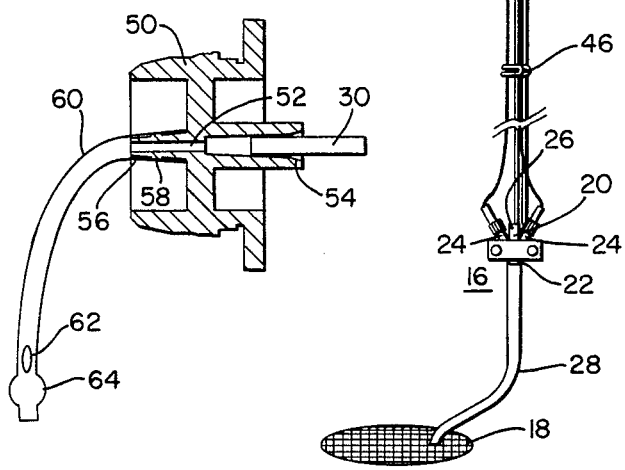
FIG. 6 is a cross-section of a container cap for use in the system illustrated in FIG. 5.

A suitable closure cap for container 12 is illustrated in cross-section in FIG. 6. Cap 50 has a central channel 52 communicating at its outer end with female Luer fitting 54. The interior of channel 52 ends in a nipple 56 which includes an annular rib 58 near its end. Metering tube 30 may be fixedly secured in female fitting 54. The interior of the channel 52 communicates with a siphon tube 60 which is solvent swelled to be placed over nipple 56, and is thereafter retained by rib 58. The inlet end of siphon tube 60 has an inlet port 62 formed in its sidewall and is weighted by BB 64 so that port 62 is positioned to accommodate outflow of substantially all liquid contents of container 12. BB 64 may be inserted in tube 60 upon swelling by solvent of the tubing, which thereafter shrinks to retain BB 64 in position.

It will be appreciated that the employment of this invention permits the predetermination of average slow delivery rates by controlling the flow resistance of the tubing secured to replaceable containers together with the predetermination of head height between the installed containers and interface 20. Integral multiples of the basic rate may be provided by the simple expedient of hanging multiple containers and connecting them to the system. Because of the flow resistance isolation of the control elements of the system, the actual mounting can be done in a variety of space situations. It is not crucial to locate the mount a specific distance above the site to which fluid is to be delivered, nor is the length of the delivery conduit crucial. A simple standard system can thus be utilized in a variety of installation site configurations. Wall space for mounting the system need not be provided at a specific location adjacent the ultimate receptacle nor at a specific vertical height above the receptacle. The system is replenished simply by replacing the empty container and attached metering tube.

Although only one embodiment of the present invention has been illustrated in the accompanying drawings and described in foregoing detailed description, it will be understood that the invention is not limited to the embodiment disclosed, but is capable of numerous rearrangements, modifications and substitutions of parts and elements without departing from the scope and spirit of the invention.

We claim:

1. Apparatus for rate-controlled gravity drip delivery of liquid from a replaceable storage container to a site comprising:
   (a) a first mount for removably suspending the container at a first elevation higher than the site;
   (b) a second mount located at a second elevation higher than the site, said second elevation being below the first elevation by a predetermined amount;
   (c) an interface secured to said second mount;
   (d) a delivery conduit extending from the interface to the site;
   (e) a metering tube of predetermined flow resistance substantially higher than that of the delivery conduit, and extending from the container to the interface, whereby a two part flow path is defined from the container to the site through the metering tube and delivery conduit; and
   (f) a flow resistance separator associated with the interface for subjecting the fluid at the interface to substantially the same ambient pressure as the fluid in the container, whereby the average rate of delivery is substantially predetermined by the difference in the first and second elevations and the flow resistance of the metering tube, and is substantially independent of the length of the delivery conduit and the distance of the container above the site.

2. The apparatus of claim 1, further including structure for delivering the liquid at integral multiples of said predetermined delivery rate wherein
   (a) the first mount removably secures a plurality of containers at said predetermined first elevation;
   (b) a plurality of container and metering tubes are suspending on said first mount; and
   (c) the interface releasably receives the downstream end of each of the plurality of metering tubes, whereby the rate of delivery to the site is equal to the predetermined rate of delivery for one container times the number of containers.

3. The apparatus of claim 1, wherein the metering tube is secured to a cap on the container, and the cap carries a weighted siphon tube having a liquid inlet remote from the cap, extending downwardly so that its liquid inlet is adjacent the bottom of the container, the siphon tube communicating through the cap to the metering tube.

4. The apparatus of claim 1, wherein the flow resistance separator comprises an air vent at the interface.

5. The apparatus of claim 4, wherein the interface comprises a manifold tubing connector having plural inlets and a single outlet.

6. For use in a system for drip delivery of liquid at a desired rate into a delivery conduit which system employs a fixed mounting of a container hanger at a predetermined vertical distance above a vented tubing connector communicating with the delivery conduit and adapted to receive the end of a metering tube, a replaceable delivery apparatus comprising:
   a flexible container containing the liquid, adapted to be suspended on said hanger; a metering tube having a predetermined flow resistance substantially larger than that of the delivery conduit, the metering tube mounted at one end on the container to communicate with the interior of the container, and being adapted at its other end to releasable securement in the tubing connector; whereby, upon hanging the container on said mounting and securing its metering tube in the connector, the liquid will be delivered from the container at a rate substantially determined by said predetermined vertical distance, and the length and cross-section of the metering tube.

7. The apparatus of claim 6, wherein the metering tube is secured to a cap on the container, and the cap carries a weighted siphon tube having a liquid inlet remote from the cap, extending downwardly so that its liquid inlet is adjacent the bottom of the container, the siphon tube communicating through the cap to the metering tube.

* * * * *